(12) United States Patent
Nezu

(10) Patent No.: US 10,874,395 B2
(45) Date of Patent: Dec. 29, 2020

(54) CLOSURE DEVICE

(71) Applicant: NIFCO INC., Yokosuka (JP)

(72) Inventor: Mikio Nezu, Yokosuka (JP)

(73) Assignee: NIFCO INC., Yokosuka (JP)

( * ) Notice: Subject to any disclaimer, the term of this patent is extended or adjusted under 35 U.S.C. 154(b) by 133 days.

(21) Appl. No.: 16/301,995

(22) PCT Filed: May 18, 2017

(86) PCT No.: PCT/JP2017/018732
§ 371 (c)(1),
(2) Date: Nov. 15, 2018

(87) PCT Pub. No.: WO2017/200058
PCT Pub. Date: Nov. 23, 2017

(65) Prior Publication Data
US 2019/0307451 A1 Oct. 10, 2019

(30) Foreign Application Priority Data

May 20, 2016 (JP) .................................. 2016-101894

(51) Int. Cl.
*A61B 17/08* (2006.01)

(52) U.S. Cl.
CPC ............ *A61B 17/085* (2013.01); *A61B 17/08* (2013.01); *A61B 2017/086* (2013.01); *A61B 2017/088* (2013.01)

(58) Field of Classification Search
CPC . A61B 17/08; A61B 17/085; A61B 2017/086; A61B 2017/088;

(Continued)

(56) References Cited

U.S. PATENT DOCUMENTS 3,926,193 A    12/1975   Hasson
8,226,668 B2 *   7/2012   Zeiner ................ A61B 17/0469
                                                               600/37

(Continued)

FOREIGN PATENT DOCUMENTS

JP      2016-503313 A    2/2016
WO    2012/151366 A2   11/2012

OTHER PUBLICATIONS

PCT/ISA/210, "International Search Report for International Application No. PCT/JP2017/018732," dated Aug. 1, 2017.

*Primary Examiner* — George J Ulsh
*Assistant Examiner* — Andrew P. Restaino
(74) *Attorney, Agent, or Firm* — Manabu Kanesaka

(57) ABSTRACT

A closure device of the present invention includes two closure elements, and two sheet materials for integrally disposing the two closure elements. Each of the closure elements includes a base portion, a drawstring portion integrally extending from the base portion, and an adjustment portion including an engaged portion having a shape engageable with the drawstring portion. The base portion of one closure element of the two closure elements and the adjustment portion of the other closure element of the two closure elements are integrally disposed on one of the sheet materials, and the adjustment portion of one closure element and the base portion of the other closure element are disposed integrally on the other of the sheet materials.

4 Claims, 9 Drawing Sheets

(58) Field of Classification Search
CPC .... A61B 2017/00407; A61B 2017/081; A61B 17/03; A61B 17/04; A61B 17/10; A61B 17/068
See application file for complete search history.

(56) References Cited

U.S. PATENT DOCUMENTS

| | | | |
|---|---|---|---|
| 2003/0092969 A1* | 5/2003 | O'Malley | A61B 17/02 600/216 |
| 2006/0095076 A1 | 5/2006 | Elliott et al. | |
| 2014/0058444 A1 | 2/2014 | Fox | |
| 2014/0236227 A1 | 8/2014 | Nash et al. | |
| 2015/0216527 A1* | 8/2015 | Belson | A61B 17/08 606/216 |
| 2016/0249924 A1* | 9/2016 | Belson | A61B 17/0466 606/216 |
| 2018/0193019 A1* | 7/2018 | Yang | A61B 17/085 |

* cited by examiner

CLOSURE DEVICE

FIELD OF TECHNOLOGY

The present invention relates to a closure device for closing a wound (an incised wound) in a skin.

BACKGROUND ART

Conventionally, as the closure device for closing (wound closure) the wound or the incised wound in the skin, there is known a closure device, for example, described in Patent Document 1. The closure device includes a base portion placed on the skin, a drawstring portion integrally extending from the base portion, and an adjustment portion placed on the skin and including an engaged portion (a ratchet mechanism) engaged with the drawstring portion. In the drawstring portion, there are formed dents and projections on an outer face, and by the dents and projections, the drawstring portion can relatively move only in one direction (a direction where the base portion and the engaged portion come close) relative to the engaged portion. Then, in a state wherein the base portion and the adjustment portion are placed (for example, attached) on the skin by sandwiching the wound of a closure object, the drawstring portion relatively moves relative to the adjustment portion so as to close the wound. As described hereinabove, since the drawstring portion can relatively move only in one direction relative to the adjustment portion, once the drawstring portion is pulled relative to the adjustment portion to close the wound, the aforementioned closure state is maintained. In such a closure device, in an initial state, a plurality of closure devices is connected in parallel, and is used by cutting for a length of the closure object according to a size of the wound.

However, in the conventional example, since a plurality of closure elements is connected so that a pulling direction of each drawstring portion becomes the same direction, a grip portion for pulling the drawstring portion is provided only on one side of the wound of the closure object. In that case, it is difficult to close the wound with an even force, so that at a time of the wound closure, there is a case wherein the wound cannot be evenly closed.

PRIOR ART DOCUMENT

Patent Document

Patent Document 1: Japanese Patent Application Publication No. 2016-503313

The present invention is made in view of the aforementioned problem. Namely, an object of the present invention is to provide a closure device which can easily close the wound evenly.

DISCLOSURE OF THE INVENTION

The present invention is a closure device for closing a wound in a skin, and the closure device comprises two closure elements, and two sheets of sheet materials for integrally disposing the two closure elements. Each of the closure elements includes a base portion; a drawstring portion integrally extending from the base portion; and an adjustment portion including an engaged portion having a shape engageable with the drawstring portion. The base portion of one closure element of the two closure elements, and the adjustment portion of the other closure element of the two closure elements are integrally disposed on one sheet material, and the adjustment portion of the one closure element and the base portion of the other closure element are integrally disposed on the other sheet material.

According to the present invention, pulling directions of the drawstring portions for closing two adjacent closure elements are opposite directions so as to provide the closure device which can easily close the wound evenly.

The two sheets of sheet materials may be respectively a surgical tape. In that case, with a simple structure, the closure device attachable to the skin can be provided.

The engaged portion may include a pair of wall portions to sandwich the drawstring portion, and the pair of wall portions may include engagement claws engageable with the drawstring portion respectively on faces thereof facing each other.

In that case, by pulling the drawstring portion from between the pair of wall portions of the engaged portion, an engagement position of the drawstring portion relative to the adjustment portion can be easily adjusted.

The drawstring portion may include a stopper portion projecting in a non-parallel direction relative to the pulling direction thereof, and the adjustment portion may include a retainer portion for preventing the drawstring portion from coming out of the adjustment portion by abutting against the stopper portion.

In that case, damaging a workability for the wound closure because the drawstring portion comes out of the adjustment portion undesirably is effectively avoided.

Alternatively, the closure device of the present invention is for closing the wound in the skin, and comprises the base portion which can be placed on a surface of the skin; the drawstring portion integrally extending from the base portion; and the adjustment portion which can be placed on the surface of the skin, and includes the engaged portion having the shape engageable with the drawstring portion, and the base portion and the adjustment portion are integrally formed.

According to the present invention, since the closure device can be formed only by one kind of parts, the closure device which can be manufactured at a low cost by a single mold can be provided. Such a closure device can be used with the single closure device by appropriately designing a separation distance between the base portion and the adjustment portion, and can be used as a closure device wherein a plurality of the closure devices is combined as described later as well. Also, since the closure device can be disposed with a high degree of freedom, the pulling direction of each drawstring portion for closing two adjacent closure devices is set in the opposite direction so as to close the wound evenly.

Preferably, a connection piece is provided between the base portion and the adjustment portion, and the connection piece connects the base portion and the adjustment portion in such a way as to change a relative position between the base portion and the adjustment portion.

In that case, since a degree of freedom to attach the base portion and the adjustment portion to the skin is high, the closure device can be suitably used for the wound closure in an area with a large radius of curvature as well.

Also, preferably, the engaged portion includes the pair of wall portions to sandwich the drawstring portion, and one wall portion of the pair of wall portions includes a guide face inclining relative to the pulling direction of the drawstring portion; and an engagement claw engageable with the drawstring portion, and the other wall portion of the pair of wall portions includes a ceiling wall to cover the drawstring portion extending in the pulling direction between the pair of wall portions, and the guide face and the ceiling wall are disposed in such a way as to pass the drawstring portion therebetween.

In that case, the drawstring portion is pulled out of a gap between the guide face and the ceiling wall so as to release an engagement between the drawstring portion and the engagement claw. Thereby, a fine adjustment of an engagement position between the drawstring portion and the adjustment portion can be easily carried out. Namely, the fine adjustment of the relative position between the base portion and the adjustment portion can be easily carried out.

Preferably, the engagement claw is an elastic claw which can be bent and deformed in the pulling direction of the drawstring portion, and the elastic claw is engageable with a concave portion of a concave-convex shape formed on a surface of the drawstring portion.

In that case, a force required for pulling the drawstring portion is small, and it does not generate a positional displacement once positioning is carried out so as to further easily adjust the engagement position between the drawstring portion and the adjustment portion. Namely, the fine adjustment of the relative position between the base portion and the adjustment portion can be further easily carried out.

The closure device comprising two or more aforementioned closure devices is included within the scope of the present invention as well. Namely, in the closure device of the present invention, the adjustment portion of one closure device is engageable with the drawstring portion of the other closure device.

According to such a closure device, at a time of the wound closure, the drawstring portion can be pulled from both directions of the wound of the closure object so as to close the wound evenly.

BEST MODES OF CARRYING OUT THE INVENTION

Hereinafter, with reference to the attached drawings, the first embodiment of the present invention will be explained in detail.

Figure 1:
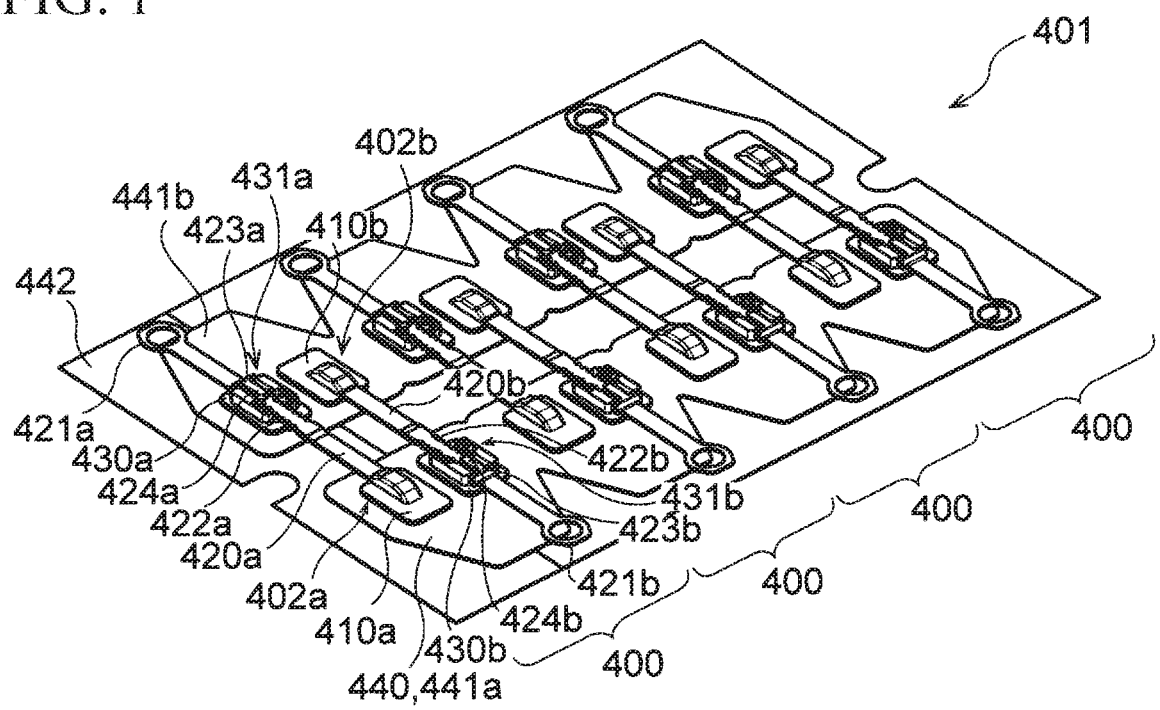
FIG. 1 is a schematic perspective view showing a closure device formed by disposing a plurality of closure devices according to the first embodiment of the present invention.
Figure 2:
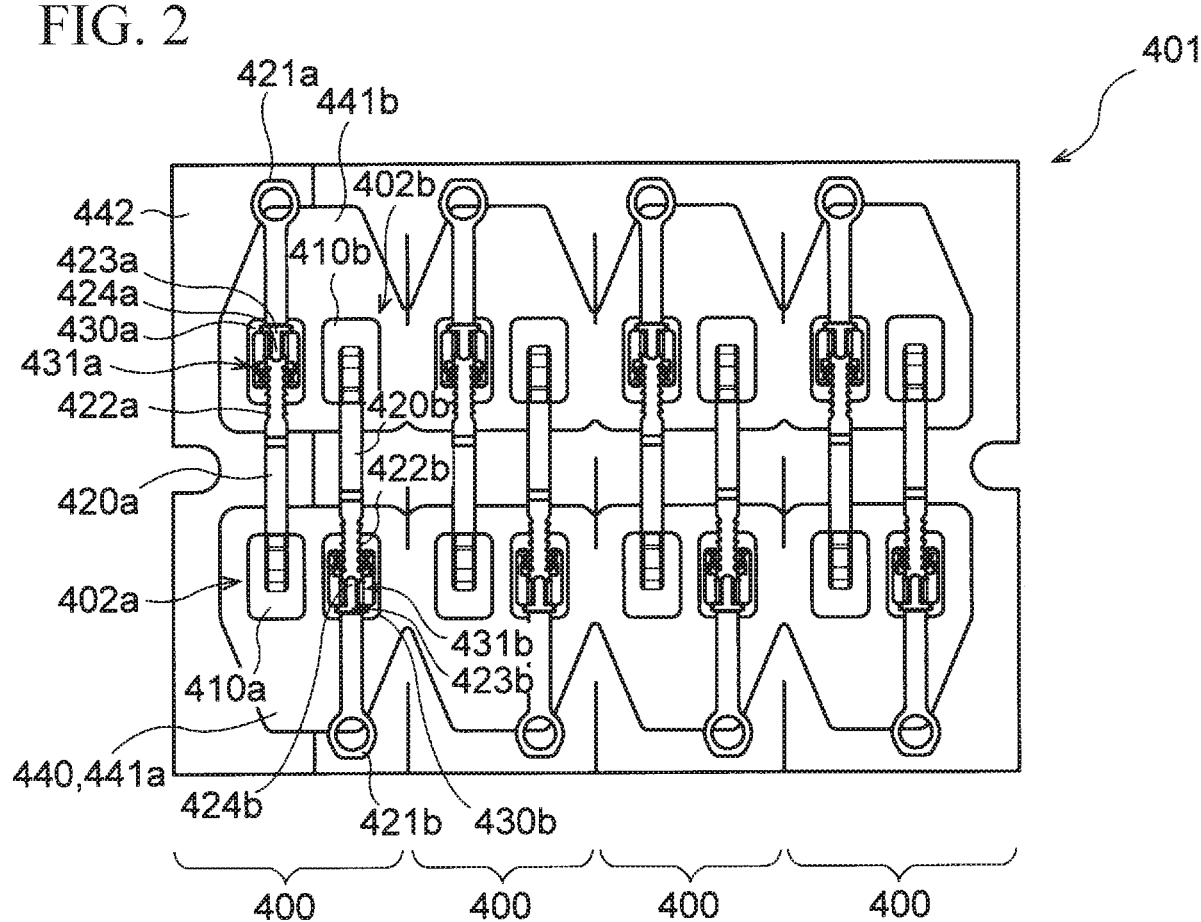
FIG. 2 is a schematic top view of the closure device in FIG. 1.
Figure 3:
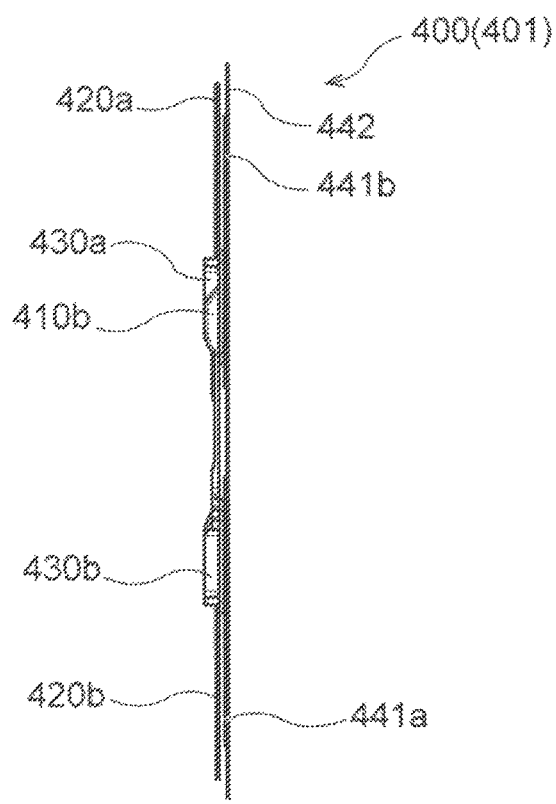
FIG. 3 is a schematic side view of the closure device in FIG. 1 viewed from a right side in FIG. 2.

FIG. 1 is a schematic perspective view showing a closure device 401 formed by disposing a plurality of closure devices 400 according to the first embodiment of the present invention. Also, FIG. 2 is a schematic top view of the closure device 401 in FIG. 1, and FIG. 3 is a schematic side view of the closure device 401 in FIG. 1 viewed from a right side in FIG. 2.

The closure device 400 according to the present embodiment is made of resin, and is for closing (wound closure) a wound such as an incised wound in a skin formed at a time of surgery, and the like. The closure device 400 comprises a first closure element 402a, a second closure element 402b, and a first sheet material 441a and a second sheet material 441b for integrally disposing the two closure elements 402a and 402b.

The first closure element 402a includes a first base portion 410a, a first drawstring portion 420a integrally extending from the first base portion 410a, and a first adjustment portion 430a including a first engaged portion 431a having a shape engageable with the first drawstring portion 420a. The second closure element 402b includes a second base portion 410a, a second drawstring portion 420a integrally extending from the second base portion 410a, and a second adjustment portion 430b including a second engaged portion 431b having a shape engageable with the second drawstring portion 420a.

Then, the first base portion 410a of the first closure element 402a, and the second adjustment portion 430b of the second closure element 402b are integrally disposed on the first sheet material 441a, and the adjustment portion 430a of the first closure element 402a and a base portion 410b of the second closure element 402b are integrally disposed on the second sheet material 441b. In the present embodiment, the first sheet material 441a and the second sheet material 441b are a surgical tape. Incidentally, in FIG. 1 and FIG. 2, the closure device 401 formed by disposing a plurality of closure devices 400 in parallel is shown.

As shown in FIG. 1 and FIG. 2, in the present embodiment, the first closure element 402a and the second closure element 402b mutually have the same structure. Therefore, in the following explanation, in a case wherein the respective closure elements 402a and 402b are not specifically distinguished, the closure elements will be collectively shown by a reference numeral 402 (without assigning signs of a and b). Also, regarding a structure element of each of the closure elements 402a and 402b as well, in a case wherein the structure element of the first closure element 402a and the structure element of the second closure element 402b are distinguished, the sign of "a" (corresponding to the first closure element) or "b" (corresponding to the second closure element) will be assigned to the end of the reference numeral, however, in the case wherein the structure elements of the first and second closure elements are not specifically distinguished, only the reference numeral will be shown without assigning the signs "a" and "b".

Figure 4:
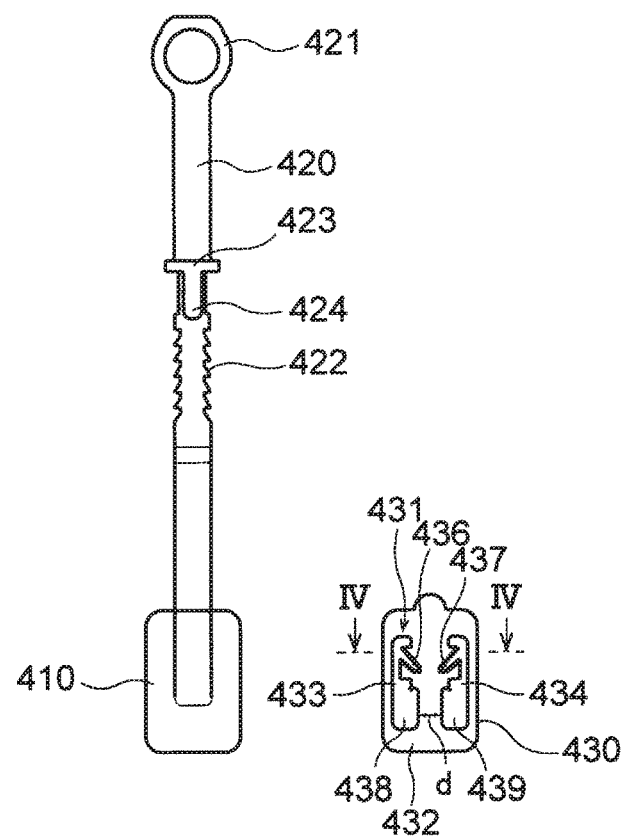
FIG. 4 is a schematic top view showing structure elements of the closure device disposed on a first sheet material in FIG. 1.

FIG. 4 is a schematic top view showing structure elements of the closure device 400 disposed on the first sheet material 441a in FIG. 1. Also, FIG. 5 is a schematic front view of the structure elements in FIG. 4, and FIG. 6 is a cross-sectional view taken along a line IV to IV in FIG. 4.

Figure 5:
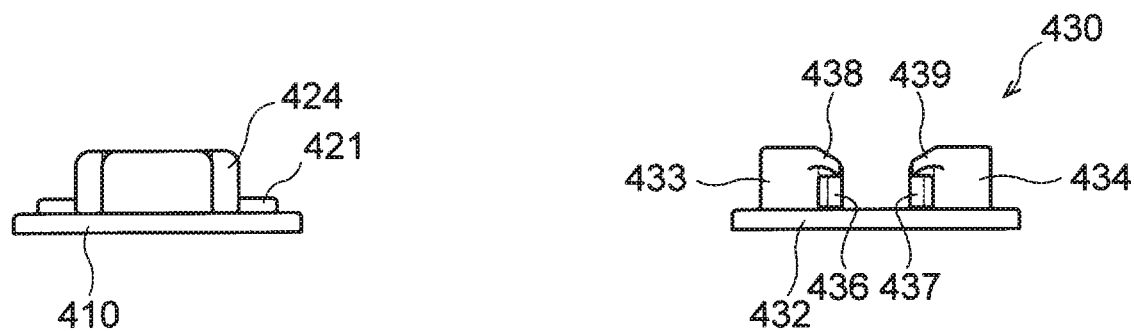
FIG. 5 is a schematic front view of the structure elements in FIG. 4.
Figure 6:
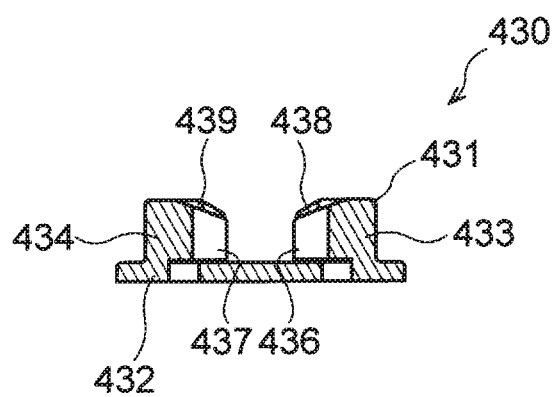
FIG. 6 is a cross-sectional view taken along a line IV-IV in FIG. 4.

As shown in FIG. 4 to FIG. 6, the base portion 410 viewed from above has an approximately rectangular shape wherein four corners are rounded, and on a face on a skin side (a face on a back side in FIG. 4, and a lower face in FIG. 5 and FIG. 6), there is provided an attachment portion (not shown in the drawings) for attaching the base portion 410 to a sheet material 441.

The drawstring portion 420 integrally formed with the base portion 410 extends from the base portion 410, and at a tip thereof, there is formed a grip portion 421. The drawstring portion 420 includes a plurality of engaging portions 422 projecting in a direction of forming an obtuse angle with respect to a pulling direction of the drawstring portion 420 on both side portions. The engaging portions 422 engage the later-described engaged portion 431 so as to define a relative position of the adjustment portion 430 relative to the base portion 410. Furthermore, the drawstring portion 420 includes a stopper portion 423 projecting in a direction orthogonal to the pulling direction thereof; and a raised portion 424 formed on an upper face of the drawstring portion 420, and having a predetermined length in a direction toward the base portion 410. As shown in FIG. 4, the stopper portion 423 and the raised portion 424 are integrally formed.

Next, the adjustment portion 430 includes an approximately rectangular flat plate 432 having a size approximately similar to that of the base portion 410. On a face on the skin side (the face on the back side in FIG. 4, and the lower face in FIG. 5 and FIG. 6) of the flat plate 432, there is provided an attachment portion (not shown in the drawings) in the same manner as in the base portion 410. The engaged portion 431 is provided on an upper face of the flat plate 432. As shown in FIG. 4, the engaged portion 431 includes a pair of wall portions 433 and 434 to sandwich the drawstring portion 420. Then, in the pair of wall portions 433 and 434, respectively on faces facing each other, there are formed engagement claws 436 and 437 engageable with the engaging portions 422 of the drawstring portion 420.

At an upper portion (a portion on a near side in FIG. 4) of the pair of wall portions 433 and 434, there are provided ceiling walls 438 and 439 to cover the drawstring portion 420 at a position (a position on a lower side in FIG. 4) moved in the pulling direction of the drawstring portion 420. The ceiling walls 438 and 439 and the pair of wall portions 433 and 434 are disposed so that the drawstring portion 420 can pass between a space surrounded by the ceiling walls 438 and 439 and the pair of wall portions 433 and 434. A separation distance d between the ceiling walls 438 and 439 is slightly wider than a width of the raised portion 424 of the drawstring portion 420, however, the separation distance d is formed to be narrower than a width of the stopper portion 423. With such a structure, the ceiling walls 438 and 439 abut against the stopper portion 423 of the drawstring portion 420 so as to function as retainer portions for preventing the drawstring portion 420 from coming out of the adjustment portion 430 undesirably.

Such closure device 400 is covered by a release paper 442 so that dirt and the like do not attach to an attachment layer provided on a back face of the sheet material 441 (surgical tape).

Such closure device 400 can be also used as the closure device 401 wherein two or more of the closure device 400 thereof are combined. Since the wound of the closure object generally has a certain degree of length, in many cases, closing the wound by the closure device 401 formed by the plurality of closure devices 400 is more efficient than closing the wound using the single closure device 400. The closure device 401 shown in FIG. 1 and FIG. 2 is formed by four closure devices 400 connected in parallel.

Next, an operation of the closure device 401 of the present embodiment will be explained. Through the explanation, an operation of the closure device 400 can be understood as well.

First, the closure device 401 is cut as necessity so that the closure device 401 corresponds to the size (length) of the wound of the closure object. The cutting is carried out along a length direction (an up-and-down direction in FIG. 2) of the drawstring portion 420, however, a position of the cutting may be located between two adjacent closure devices 400, or between the first closure element 402a and the second closure element 402b included in one closure device 400 as well.

In an initial state, the stopper portion 423 of the drawstring portion 420 abuts against an edge portion of the ceiling walls 438 and 439 of the adjustment portion 430, and the raised portion 424 is located between the ceiling walls 438 and 439. With such a structure, the drawstring portion 420 does not move in a direction opposite to the pulling direction relative to the adjustment portion 430 so as to prevent the drawstring portion 420 from coming out of the adjustment portion 430.

Next, the release paper 442 covering the back face of the sheet material 441 is peeled off so as to expose the attachment portion formed on the back face of the sheet material 441. Then, the closure device 401 is attached onto the skin such that the first sheet material 441a and the second sheet material 441b are positioned by sandwiching the wound of the closure object. Prior to the attachment, in order to enhance an attachment property of the attachment portion of the sheet material 441 relative to the skin, it is preferable to clean and dry the surface of the skin as an attachment object beforehand. This attachment operation is carried out over an entire length of the wound of the closure object. Incidentally, the closure device 401 can be placed in an area with a small radius of curvature as well. In that case, the sheet material 441 bends and becomes deformed so as to suitably correspond to a shape in the area of the attachment object.

Then, a first grip portion 421a of the first drawstring portion 420a of the first closure element 402a and a second grip portion 421b of the second drawstring portion 420b of the second closure element 402b are pulled simultaneously. Thereby, since each drawstring portion 420 moves in the pulling direction respectively relative to the corresponding engaged portion 431, a substantially equal force acts on a body tissue around the wound. By the aforementioned pulling operation, the base portion 410 and the adjustment portion 430 come close. Namely, by the first and second sheet materials 441a and 441b, the body tissue around the wound moves so as to close the wound. The pulling operation is carried out so that a force necessary and sufficient for closing the wound is applied to the body tissue around the wound.

When the drawstring portion 420 moves in the pulling direction relative to the engaged portion 431, convex portions of the engaging portions 422 of the drawstring portion 420 pass the engagement claws 436 and 437 while bending and deforming the engagement claws 436 and 437 in the pulling direction. On the other hand, when the engaging portions 422, moved in the pulling direction beyond the engagement claws 436 and 437, are attempted to move in the direction opposite to the pulling direction, the convex portions thereof interfere with the engagement claws 436 and 437 so as to control a movement of the drawstring portion 420. As mentioned above, this is because while a curvature deformation in the pulling direction is relatively easy since the engagement claws 436 and 437 curve toward the pulling direction, the curvature deformation in the direction opposite to the pulling direction is impossible as a matter of practice. In this manner, the movement of the drawstring portion 420 is allowed only in the pulling direction.

Such a pulling operation of the grip portion 421 (drawstring portion 420) is carried out in all of the closure devices 400. Thereby, the wound of the closure object is completely closed. Then, in the drawstring portion 420, the area pulled out beyond the engagement claws 436 and 437 by the pulling operation is cut by a suitable cutting tool. Thereby, the closure of the wound by the closure device 401 is completed.

By maintaining this closure state in a fixed period, body tissues separated by the wound join to each other so as to heal the wound. Thereafter, the sheet material 441 is removed from the skin.

According to the present embodiment as described above, the closure device 400 which can easily close the wound evenly by setting the pulling direction of each drawstring portion 420 for closing the two adjacent closure elements 402 to be the opposite direction, can be provided.

In the present embodiment, the surgical tape is selected respectively as two sheets of sheet materials 441a and 441b. Consequently, with the simple structure, the closure device 400 which can be attached onto the skin can be provided.

Also, the engaged portion 431 includes the pair of wall portions 433 and 434 to sandwich the drawstring portion 420, and the pair of wall portions 433 and 434 includes the engagement claws 436 and 437 engageable with the engaging portions 422 of the drawstring portion 420 respectively on the faces facing each other. Consequently, by pulling the drawstring portion 420 from between the pair of wall portions 433 and 434, an engagement position between the drawstring portion 420 and the adjustment portion 430 can be easily adjusted.

Furthermore, the drawstring portion 420 includes the stopper portion 423 projecting in the direction orthogonal to the pulling direction thereof, and the ceiling walls 438 and 439 of the adjustment portion 430 abut against the stopper portion 423 so as to prevent the drawstring portion 420 from coming out of the adjustment portion 430. Consequently, damaging a workability of the wound closure because the drawstring portion 420 comes out of the adjustment portion 430 undesirably is effectively avoided.

Incidentally, the first drawstring portion 420a and the second drawstring portion 420b do not necessarily have to be disposed so as to become parallel to each other. In the present embodiment, when the closure device 400 is prepared, the base portion 410 and the adjustment portion 430 are attached onto the two sheets of sheet materials 441a and 441b. At that time, in order to carry out the closure of the wound most effectively, the first drawstring portion 420a and the second drawstring portion 420b may be disposed to become non-parallel to each other according to a radius of curvature and the like of the skin around the wound of the closure object.

Next, a closure device 100 according to a second embodiment of the present invention will be explained.

Figure 7:
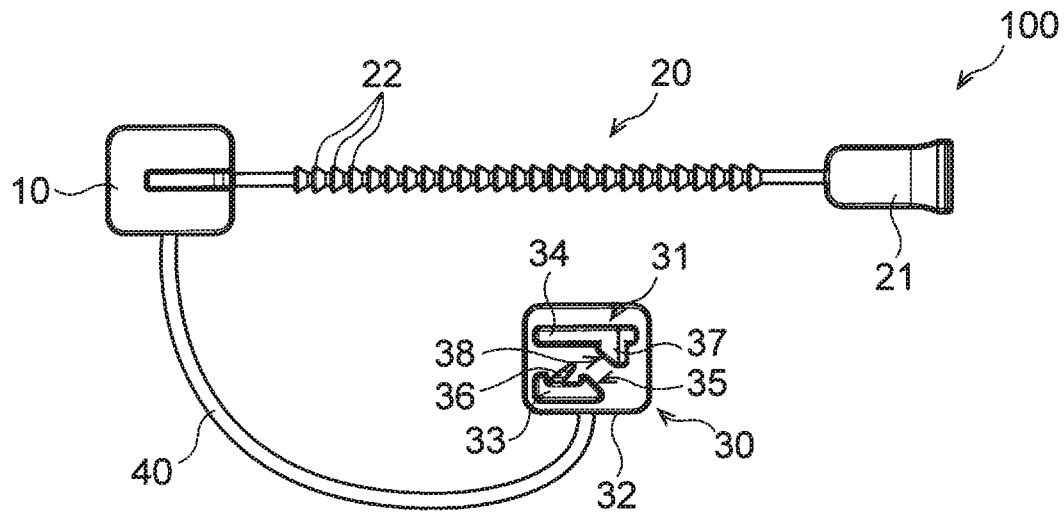
FIG. 7 is a schematic top view showing the closure device according to a second embodiment of the present invention.

FIG. 7 is a schematic top view showing the closure device 100 according to the second embodiment of the present invention. The closure device 100 is also made of resin, and is for closing (wound closure) the wound such as the incised wound of the skin formed at the time of surgery, and the like. The closure device 100 comprises a base portion 10 which can be placed on the surface of the skin; a drawstring portion 20 integrally extending from the base portion 10; and an adjustment portion 30 which can be placed on the surface of the skin, and includes an engaged portion 31 having a shape engageable with the drawstring portion 20.

The base portion 10 viewed from above has an approximately rectangular shape wherein four corners are rounded, and on a face placed on the skin (a reverse face in FIG. 7), there is provided an attachment portion (not shown in the drawings) for attaching the base portion 10 to the skin. In the initial state, the attachment portion is covered by the release paper and the like so as not to attach to the attachment portion of another closure device and the like undesirably. The drawstring portion 20 integrally formed with the base portion 10 extends from the base portion 10, and at a tip thereof, there is formed a grip portion 21. In the drawstring portion 20, there are formed concave and convex portions on an outer face. The concave and convex portions are formed on a surface of the drawstring portion 20 by continuously forming concave-convex elements 22 having a minute truncated cone shape tapering toward the pulling direction (a rightward direction in FIG. 7) of the drawstring portion. Namely, a space sandwiched by two adjacent concave-convex elements 22 in the pulling direction is a concave portion, and an outer diameter portion of a bottom face of the concave-convex elements 22 is a convex portion. The concave portion is engageable with the later-described engaged portion 31, and serves a role of regulating a relative position of the adjustment portion 30 relative to the base portion 10.

The adjustment portion 30 of the present embodiment includes an approximately rectangular flat plate 32 having a size approximately similar to that of the base portion 10. On a face on a side placed on the skin in the flat plate 32 (the reverse face in FIG. 7), there is provided the attachment portion (not shown in the drawings) in the same manner as in the base portion 10. On the other hand, the engaged portion 31 is provided on an upper face of the flat plate 32. The engaged portion 31 includes a pair of wall portions 33 and 34 to sandwich the drawstring portion 20. One wall portion 33 of the pair of wall portions includes a guide face 35 inclining with respect to the pulling direction of the drawstring portion 20, and an engagement claw 36 engageable with the drawstring portion 20. On the other hand, the other wall portion 34 of the pair of wall portions includes a ceiling wall 37 to cover the drawstring portion 20 at a position facing the guide face 35. The ceiling wall 37 and the guide face 35 are disposed so that the drawstring portion 20 can pass therebetween. In other words, a separation distance between the guide face 35 and the ceiling wall 37 is larger than the maximum value of an outer diameter of the conical concave-convex elements 22 provided in the drawstring portion 20.

In the present embodiment, the pair of wall portions 33 and 34 extends approximately vertically up to a height beyond an outer diameter of the drawstring portion 20 from the upper face of the flat plate 32, and has a predetermined length respectively along the pulling direction of the drawstring portion 20.

Figure 9:
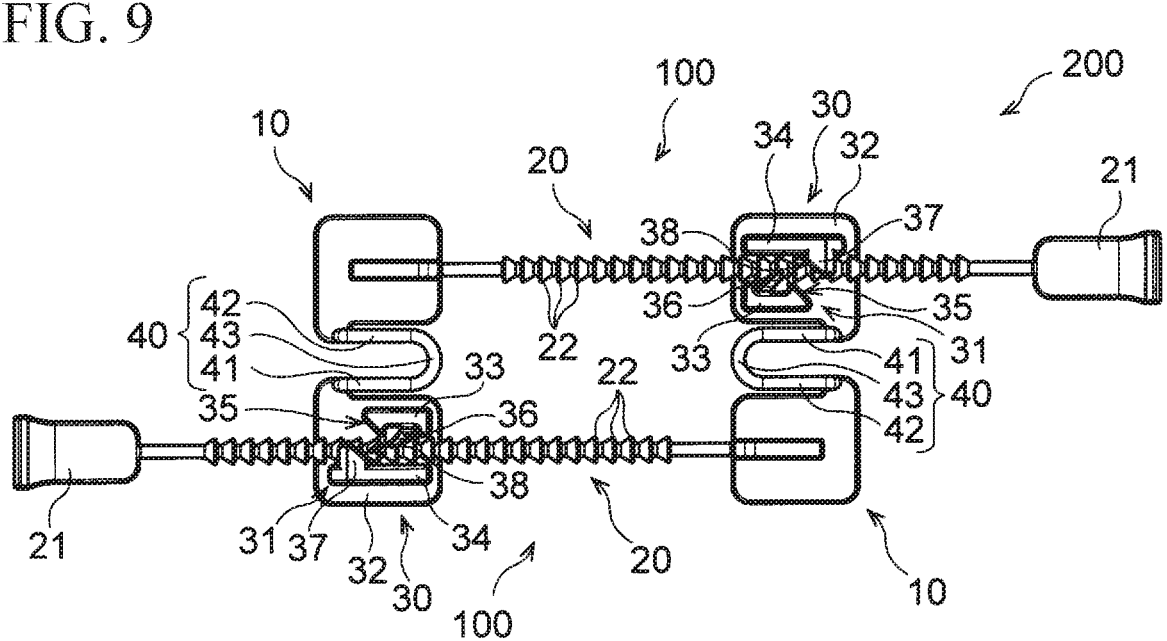
FIG. 9 is a schematic top view showing the closure device in FIG. 8.

The guide face 35 is for guiding the drawstring portion 20 when the drawstring portion 20 is removed from the engaged portion 31. A method of removing the drawstring portion 20 from the engaged portion 31 will be described later. The guide face 35 is provided at an end portion on a pulling direction side of the drawstring portion 20 in one wall portion 33, and forms an acute angle with respect to the pulling direction. Also, the engagement claw 36 extends toward the other wall portion 34 from one wall portion 33, and curves in the pulling direction while tapering. On the other hand, the ceiling wall 37 is provided on a pulling direction side of the other wall portion 34, and as shown in FIG. 9, when viewed from above, the ceiling wall 37 has a right-angled triangle shape. In the present embodiment, an edge portion 38 corresponding to a hypotenuse of the right-angled triangle is parallel to the guide face 35. The ceiling wall 37 of the present embodiment is provided above the drawstring portion 20 so as not to interfere with the drawstring portion 20 when the drawstring portion 20 is pulled (see FIG. 12).

Also, in the present embodiment, as shown in FIG. 7, the base portion 10 and the adjustment portion 30 are integrally formed through a connection piece 40. Thereby, the base portion 10, the drawstring portion 20, the adjustment portion 30, and the connection piece 40 are integrally formed. With the aforementioned structure, the present closure device 100 can be integrally molded by a single mold. The connection piece 40 has flexibility, and the base portion 10 and the adjustment portion 30 can be disposed respectively at a desired position by sandwiching the wound of the closure object. Furthermore, even if the base portion 10 and the adjustment portion 30 are disposed on the skin of a joint part, they can follow a movement of the joint.

Such closure device 100 can be also used with only one, however, the closure device 100 can be used by combining two or more closure devices 100 as a closure device 200 as well. Since the wound of the closure object generally has a certain degree of length, in many cases, closing the wound by the closure device 200 comprising a plurality of closure devices 100 is more efficient than closing the wound using the single closure device 100. Such closure device 200 will be explained hereinafter as a third embodiment of the present invention. Through the third embodiment, an operation of the closure device 100 according to the second embodiment can be understood as well.

Figure 8:
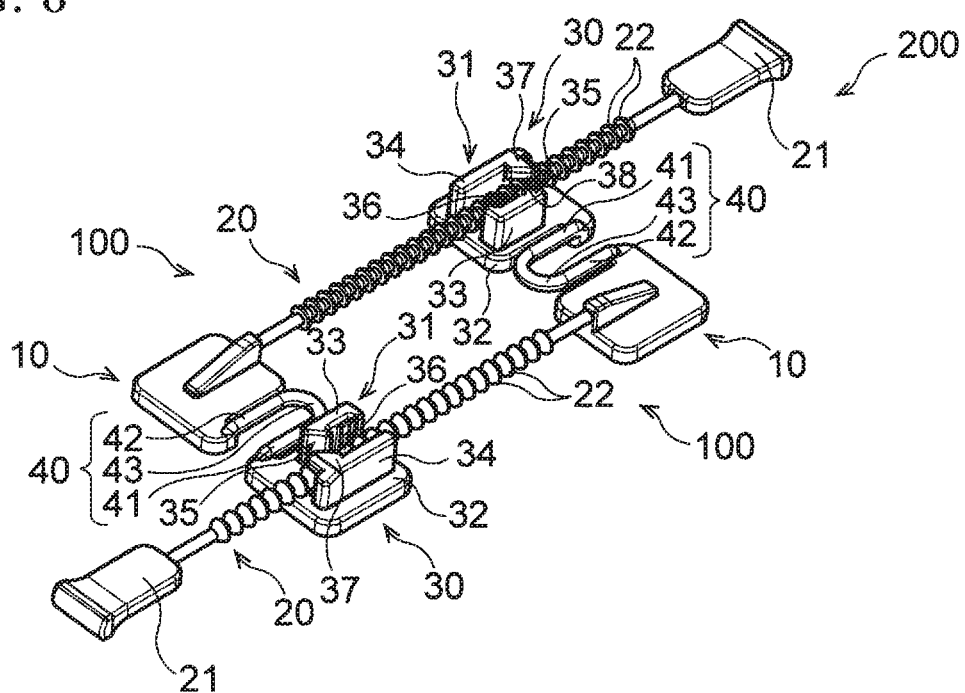
FIG. 8 is a schematic perspective view showing the closure device formed by combining two closure devices in FIG. 7.
Figure 10:
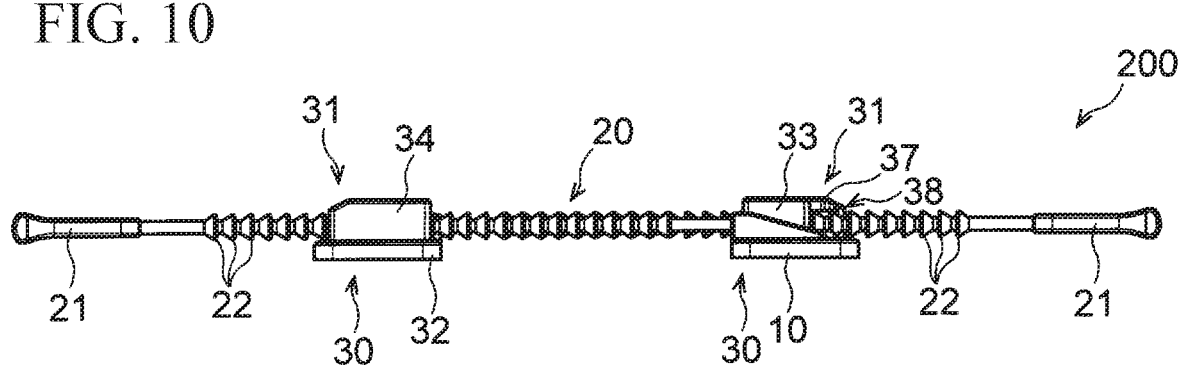
FIG. 10 is a schematic side view showing the closure device viewed from below in FIG. 9.
Figure 11:
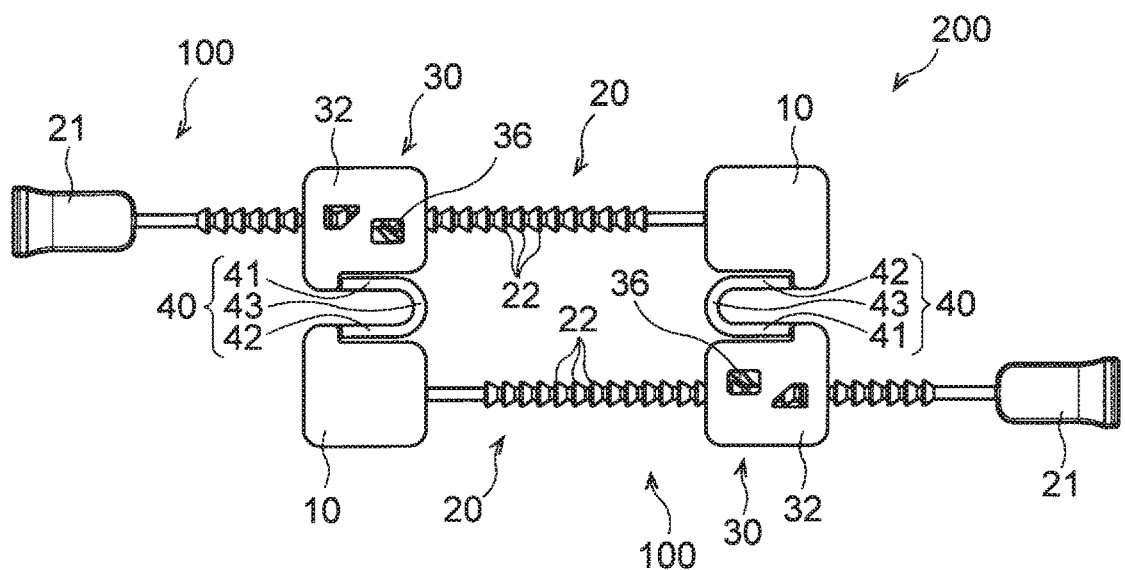
FIG. 11 is a schematic bottom view showing the closure device in FIG. 8.
Figure 12:
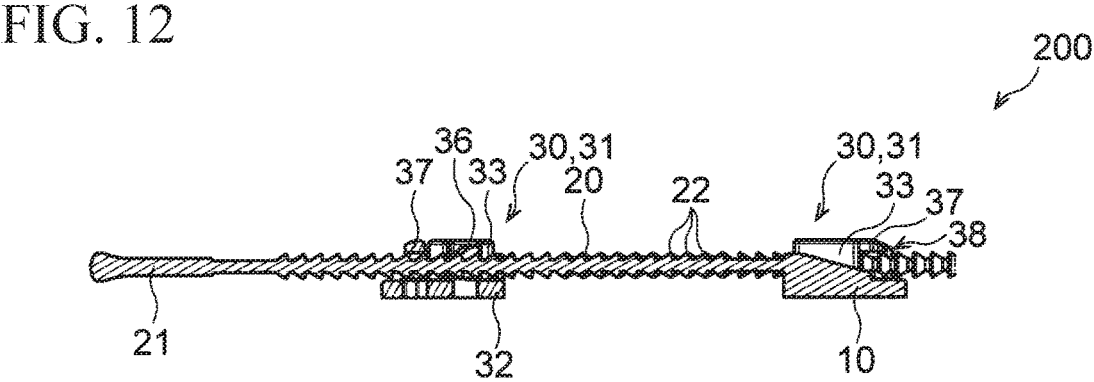
FIG. 12 is a cross-sectional view taken along a line A-A in FIG. 9.
Figure 13:
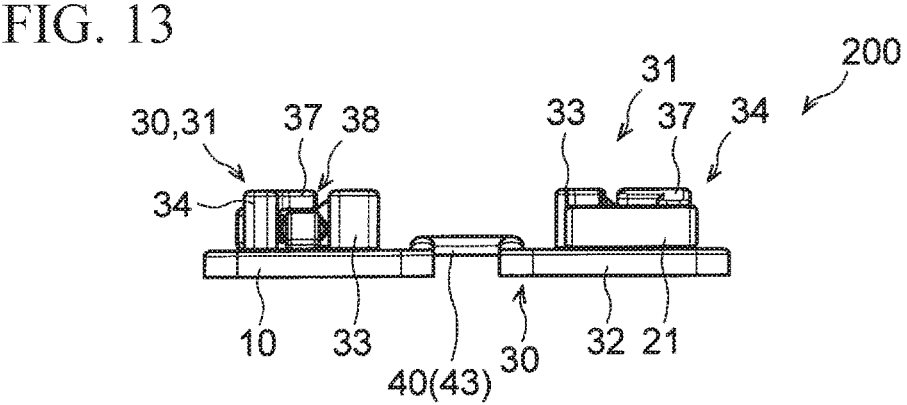
FIG. 13 is a schematic front view showing the closure device viewed from a right side in FIG. 9.

FIG. 8 is a schematic perspective view showing the closure device 200 formed by combining two closure devices 100 according to the second embodiment. Also, FIG. 9 is a schematic top view showing the closure device 200 in FIG. 8; FIG. 10 is a schematic side view showing the closure device 200 viewed from below in FIG. 9; FIG. 11 is a schematic bottom view showing the closure device 200 in FIG. 8; FIG. 12 is a cross-sectional view taken along a line A to A in FIG. 9; and FIG. 13 is a schematic front view showing the closure device 200 viewed from a right side in FIG. 9.

As shown in FIG. 8 to FIG. 13, in the closure device 200 of the present embodiment, two of the closure devices 100 shown in FIG. 7 are prepared and assembled to face each other so as to have different pulling directions of the drawstring portion of each closure device 100 by 180 degrees respectively. Specifically, the drawstring portion 20 of one closure device 100 engages the engaged portion 31 provided in the adjustment portion 30 of the other closure device 100, and furthermore, the drawstring portion 20 of the other closure device 100 engages the engaged portion 31 provided in the adjustment portion 30 of one closure device 100.

In the present embodiment, in each closure device 100, the connection piece 40 connecting the base portion 10 and the adjustment portion 30 has a U shape including first and second leg portions 41 and 42 parallel to each other, and a folded portion 43 which can be bent and deformed to connect the first and second leg portions 41 and 42.

Next, an operation of the closure device 200 of the present embodiment will be explained.

First, the closure device 200 formed by combining two closure devices 100 is prepared with a required number according to a size of the wound of the closure object. Then, the attachment portions provided on the reverse faces of the base portion 10 and the adjustment portion 30 are exposed, and the base portion 10 and the adjustment portion 30 are attached onto the skin by sandwiching the wound of the closure object. Prior to the attachment, in order to allow the attachment portion to be easily attached to the skin, it is preferable to clean and dry the surface of the skin as the attachment object beforehand. This attachment operation is carried out over the entire length of the wound of the closure object. Incidentally, the closure device 200 can also be placed in the area with the small radius of curvature. In that case, the U-shaped connection piece 40 connecting the base portion 10 and the adjustment portion 30 bends and becomes deformed so as to suitably correspond to the shape in the area of the attachment object.

Then, the grip portions 21 of two drawstring portions 20 provided in the closure device 200 are pulled simultaneously in the opposite directions. Thereby, each drawstring portion 20 moves in the pulling direction respectively relative to the corresponding engaged portion 31, and the base portion 10 and the adjustment portion 30 come close. Namely, the body tissue around the wound moves in such a way as to close the wound. The aforementioned pulling operation is carried out so that the force necessary and sufficient for closing the wound is applied to the body tissue around the wound. There, by the presence of the engagement claw 36, the drawstring portion 20 can move only in the pulling direction, and cannot move in the opposite direction thereof. Specifically, when the drawstring portion moves in the pulling direction relative to the engaged portion 31, an inclined face of the conical concave-convex elements 22 forming the drawstring portion 20 passes the engagement claw 36 while bending and deforming the engagement claw 36 in the pulling direction. On the other hand, when the concave-convex elements 22 moved in the pulling direction beyond the engagement claw 36 is attempted to move in the direction opposite to the pulling direction, the bottom face of the conical concave-convex elements 22 interferes with the engagement claw 36 so as to control the movement thereof. As mentioned above, this is because while a further curvature deformation in the pulling direction is relatively easy since the engagement claw 36 curves toward the pulling direction, the curvature deformation in the direction opposite to the pulling direction is impossible as a matter of practice. In this manner, the movement of the drawstring portion 20 is allowed only in the pulling direction.

Such pulling operation of the grip portion 21 (drawstring portion 20) is carried out in all of the closure device 200. Thereby, the wound of the closure object is completely closed. Then, in the drawstring portion 20, the area pulled out beyond the engagement claw 36 by the pulling operation is cut by the suitable cutting tool. Thereby, the closure of the wound by the closure device 200 is completed.

By maintaining this closure state in the fixed period, the body tissues separated by the wound join each other so that the wound disappears. Thereafter, the base portion 10 and the adjustment portion 30 are removed from the skin.

In the closure device 200 of the present embodiment, it is also easy to modify or finely adjust the separation distance between the base portion 10 and the adjustment portion 30. For example, in a case wherein the drawstring portion 20 is excessively pulled relative to the adjustment portion 30, the drawstring portion 20 may be removed from the engaged portion 31. For this purpose, the drawstring portion 20 is bent along the guide face 35, and in that state, by pulling the drawstring portion 20 upwardly, the drawstring portion 20 may pass through a gap between the guide face 35 and the ceiling wall 37. In this way, by removing the drawstring portion 20 from the engaged portion 31, an adjustment of the separation distance between the base portion 10 and the adjustment portion 30 can be carried out desirably. Then, when the adjustment of the separation distance is completed, the drawstring portion 20 is disposed between the pair of wall portions 33 and 34 again from the gap between the guide face 35 and the ceiling wall 37. Namely, the concave-convex elements 22 of the drawstring portion 20 engage the engagement claw 36 of the engaged portion 31, and the separation distance between the base portion 10 and the adjustment portion 30 is fixed. In a case wherein the separation distance between the base portion 10 and the adjustment portion 30 is still inadequate, the same adjustment operation may be repeated.

According to the closure device 200 described above, since the closure device 200 can be formed only by one kind of component, in a case wherein the closure device 200 is manufactured by injection molding of a synthetic resin, the closure device 200 can be manufactured by the single mold. Consequently, a manufacturing cost can be reduced more than a conventional device. Incidentally, in a case wherein the closure device 200 is manufactured by the injection molding, in consideration of the flexibility, a chemical resistance, and a sterilizing treatment, it is preferable to use PA12 as a raw material. Obviously, the raw material is not limited to the above, and may use other raw materials.

Also, the connection piece 40 is provided between the base portion 10 and the adjustment portion 30, and the connection piece 40 connects the base portion 10 and the adjustment portion 30 in such a way as to change the relative position between the base portion 10 and the adjustment portion 30. Consequently, a degree of freedom to attach the base portion 10 and the adjustment portion 30 to the skin is high, and the closure device 200 can be suitably used for the area with the large radius of curvature as well. Furthermore, even in a case wherein the closure device 200 is used for the joints such as a knee, the elbow, and the like, since the connection piece 40 can be bent and deformed, the base portion 10 and the adjustment portion 30 can follow the movement of the joint portion.

Also, the engaged portion 31 includes the pair of wall portions 33 and 34 to sandwich the drawstring portion 20; one wall portion 33 includes the guide face 35 inclining with respect to the pulling direction of the drawstring portion 20, and the engagement claw 36 engageable with the drawstring portion 20; and the other wall portion 34 includes the ceiling wall 37 to cover the drawstring portion 20 extending in the pulling direction between the pair of wall portions 33 and 34. Then, the guide face 35 and the ceiling wall 37 are disposed such that the drawstring portion 20 can pass through between the pair of wall portions 33 and 34. Therefore, by pulling the drawstring portion 20 through the gap between the guide face 35 and the ceiling wall 37, the engagement between the drawstring portion 20 and the engagement claw 36 can be released. Thereby, it is easy to modify or finely adjust an engagement position between the drawstring portion 20 and the engaged portion 31. Namely, it is easy to modify or finely adjust the relative position between the base portion 10 and the adjustment portion 30.

Furthermore, the engagement claw 36 is an elastic claw which can be bent and deformed in the pulling direction of the drawstring portion 20, and the elastic claw can engage a concave portion of a concave-convex shape formed on the surface of the drawstring portion 20. Consequently, a small force is required for pulling the drawstring portion 20, and it does not cause a positional misalignment once the positioning is carried out, so that it is further easy to adjust the engagement position between the drawstring portion 20 and the adjustment portion 30. Namely, it is further easy to modify or finely adjust the relative position between the base portion 10 and the adjustment portion 30.

Obviously, respective effects with respect to the closure device 200 described herein correspond to the single closure device 100 according to the second embodiment as well.

Incidentally, here, as for the closure device 100 forming the closure device 200, an example including each one of the base portion, the adjustment portion, and the drawstring portion has been explained, however, obviously, two or more of the base portion, the adjustment portion, and the drawstring portion may be included respectively. For example, in a case wherein each four of the base portion, the adjustment portion, and the drawstring portion are included, the base portion and the adjustment portion may be integrally molded two by two alternately through the U-shaped connection piece, and each one drawstring portion may extend in the same direction parallel to each other from two base portions. Two closure devices are prepared, and in a state wherein the pulling directions of the drawstring portions of the respective closure devices face each other so as to have different directions by 180 degrees respectively, the drawstring portion of one closure device may engage the engaged portion provided in the adjustment portion corresponding to the other closure device, and in the same manner, the drawstring portion of the other closure device may engage the engaged portion provided in the adjustment portion corresponding to one closure device.

Incidentally, it is also effective to apply the structure of the engaged portion 31 employed in the closure device 100 and the closure device 200 described hereinabove to the closure device formed by two members wherein the adjustment portion is formed in a different member from the base portion. Such closure device 300 will be explained with reference to FIG. 14 to FIG. 19.

Figure 14:
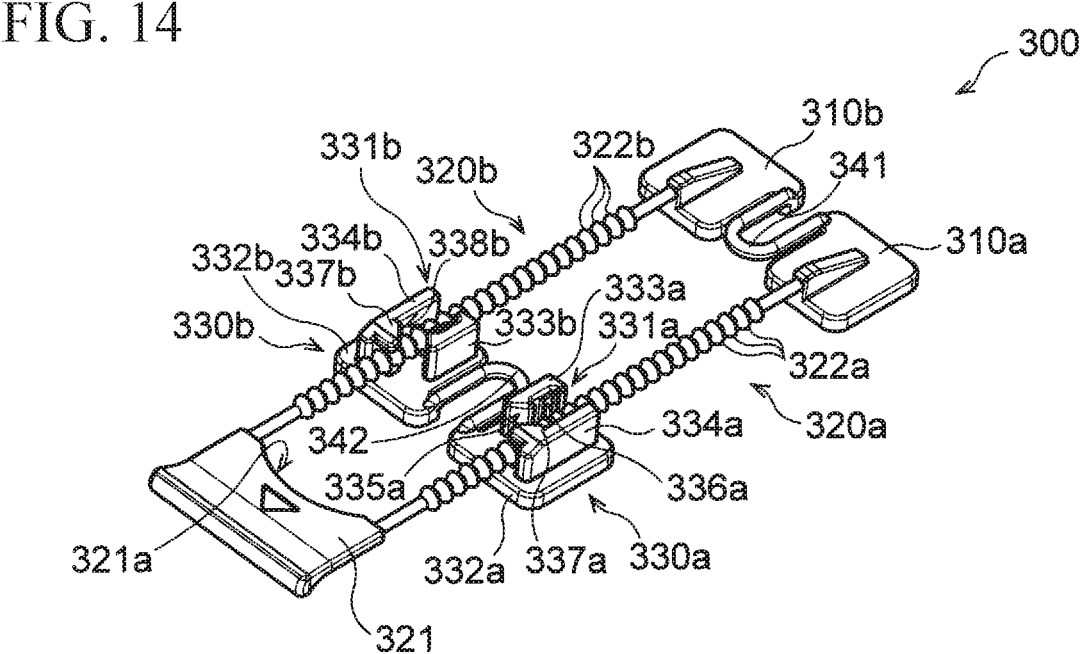
FIG. 14 is a schematic perspective view showing the closure device formed by two members including an adjustment portion of the present invention.
Figure 15:
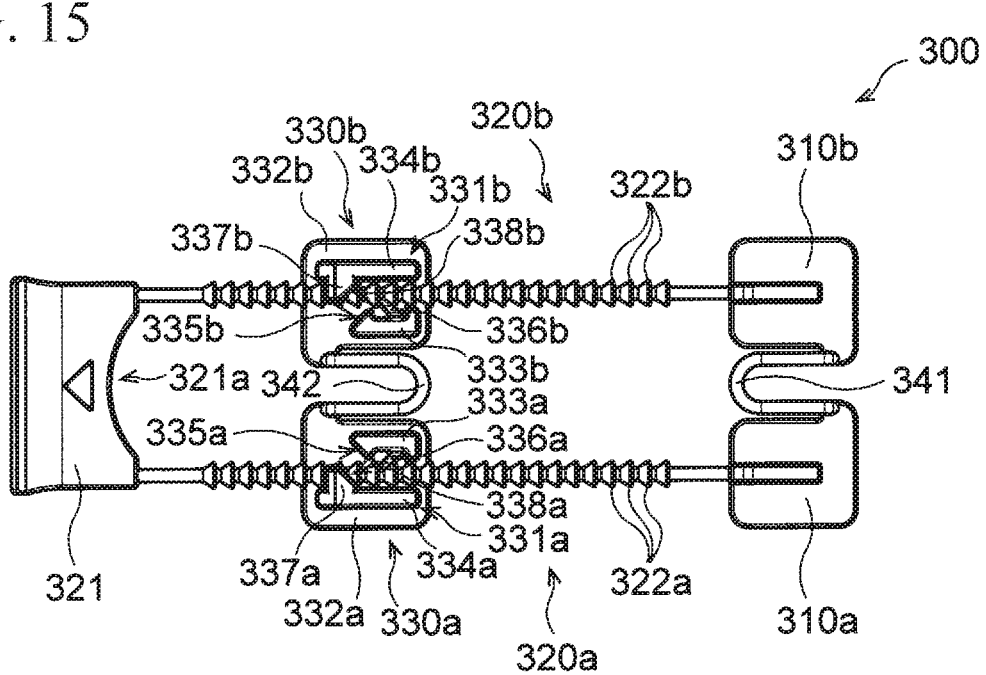
FIG. 15 is a schematic top view showing the closure device in FIG. 14.
Figure 16:
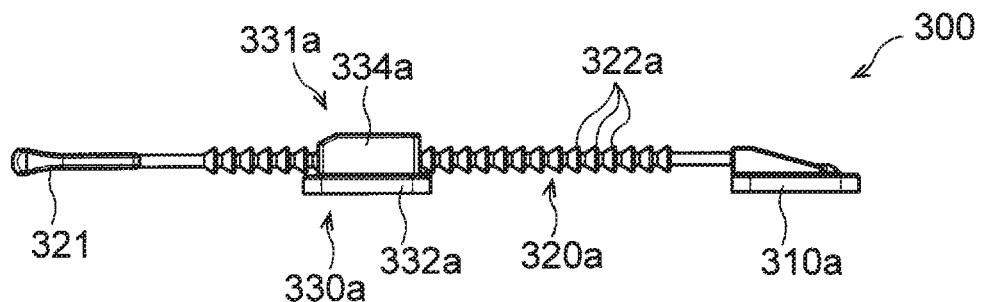
FIG. 16 is a schematic side view showing the closure device viewed from below in FIG. 15.
Figure 17:
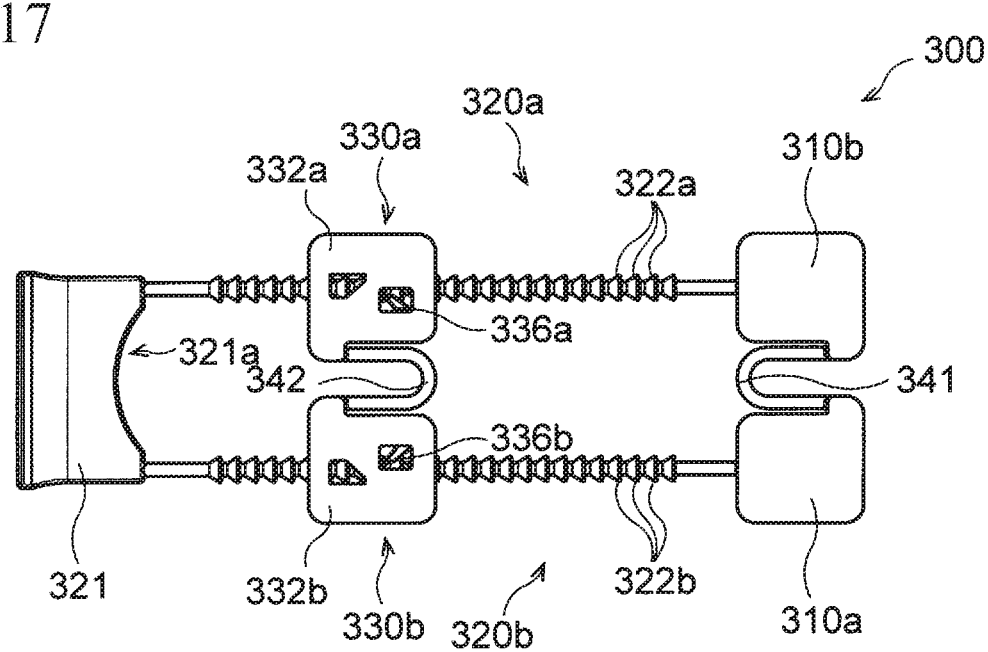
FIG. 17 is a schematic bottom view showing the closure device in FIG. 14.
Figure 18:
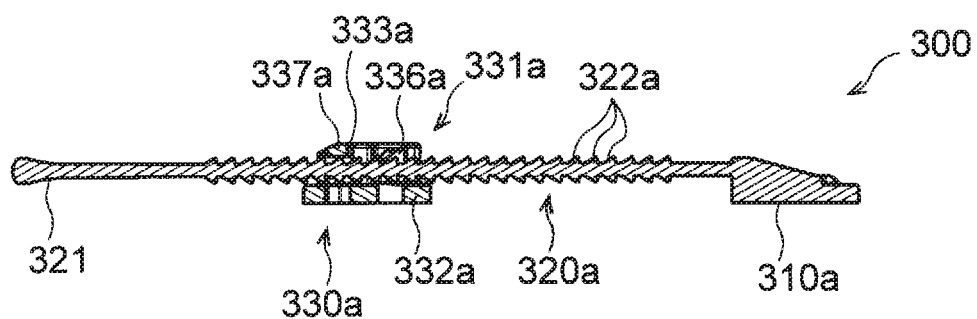
FIG. 18 is a cross-sectional view taken along a line A-A in FIG. 15.
Figure 19:
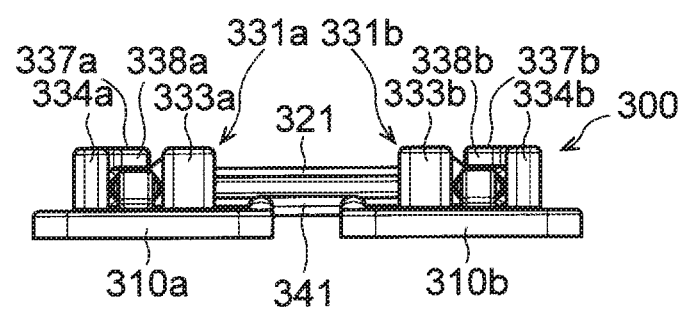
FIG. 19 is a schematic front view showing the closure device viewed from a right side in FIG. 15.

FIG. 14 is a schematic perspective view showing a closure device 300 comprising the two members including the aforementioned adjustment portion; FIG. 15 is a schematic top view showing the closure device 300 in FIG. 14; FIG. 16 is a schematic side view showing the closure device 300 viewed from below in FIG. 15; FIG. 17 is a schematic bottom view showing the closure device 300 in FIG. 14; FIG. 18 is a cross-sectional view taken along a line A-A in FIG. 15; and FIG. 19 is a schematic front view showing the closure device 300 viewed from a right side in FIG. 15.

As shown in FIG. 14 to FIG. 19, the closure device 300 comprises a first member 301 including two base portions 310a and 310b connected through a first connection piece 341, each one of drawstring portions 320a and 320b extending from an upper face of each of the base portions 310a and 310b, and a grip portion 321 connecting a tip portion of each of the drawstring portions 320a and 320b; and a second member 302 formed by two adjustment portions 330a and 330b connected through a second connection piece 342. As shown in the drawings, the respective drawstring portions 320a and 320b extend in parallel to each other.

Although it is not shown in the drawings, on a bottom face (a face on a near side in FIG. 17) of each of the base portions 310a and 310b, and each of the adjustment portions 330a and 330b, there are provided attachment portions respectively in the same manner as in the aforementioned closure device 100 and closure device 200.

Also, the grip portion 321 has an approximately rectangular shape viewed from above, however, one side on the base portions 310a and 310b, there is formed an arch-shaped edge portion 321e curved toward an inside of the rectangular shape. The arch-shaped edge portion 321e is suitably caught on a finger of a user when using the closure device 300 so as to improve usability. Furthermore, the grip portion 321 has a function of maintaining a parallel state of the two drawstring portions 320a and 320b as well in addition to a function as a holding portion when using the closure device 300.

The first and second connection pieces 341 and 342 of the closure device 300 are U-shaped members having flexibility in the same manner as in the aforementioned closure device 100 and closure device 200. As shown in FIG. 14, FIG. 15, and FIG. 17, the respective connection pieces 341 and 342 are disposed so as to have a phase different by 180 degrees with each other. Furthermore, the second member 302 is disposed in a mirror symmetry in a direction wherein each one of the wall portions 333a and 333b of each one pair of the wall portions 333a, 334a, 333b, and 334b provided in each of the adjustment portions 330a and 330b comes to a proximal position to each other. With the aforementioned structure, in a state wherein the first member 301 and the second member 302 are combined (see FIG. 14 to FIG. 19), the closure device 300 has a shape symmetrical (mirror symmetry) with respect to a flat surface parallel to the respective drawstring portions 320a and 320b and having an equal distance from the respective drawstring portions 320a and 320b.

Each of the base portions 310a and 310b, each of the drawstring portions 320a and 320b, and each of the adjustment portions 330a and 330b in the closure device 300 have the same structure as the aforementioned closure device 100 and closure device 200. Therefore, in FIG. 14 to FIG. 19, substantially similar symbols are assigned to component parts corresponding to the closure device 100 and the closure device 200, and detailed explanations thereof are omitted.

A method of closing the wound of the closure object using the closure device 300 comprises the following processes. Namely, first, the closure device 300 is provided with the required number according to the size of the wound of the closure object. Then, the attachment portions provided on the reverse faces of the base portions 310a and 310b, and the adjustment portions 330a and 330b are exposed, and the base portions 310a and 310b, and the adjustment portions 330a and 330b are attached onto the skin by sandwiching the wound of the closure object. As mentioned above, prior to the attachment, in order to allow the attachment portions to be easily attached to the skin, it is preferable to clean and dry the surface of the skin as the attachment object beforehand.

This attachment operation is carried out over the entire length of the wound of the closure object. The closure device 300 can also be placed in the area with the small radius of curvature. That is because the U-shaped connection pieces 341 and 342 connecting the base portions 310a and 310b, and the adjustment portions 330a and 330b bend and become deformed so as to suitably correspond to the shape in the area of the attachment object.

Then, the grip portion 321 provided in the closure device 300 is pulled in one direction. Since the grip portion 321 connects two drawstring portions 320a and 320b, at that time, the two drawstring portions 320a and 320b are simultaneously pulled. Thereby, the respective drawstring portions 320a and 320b move in the pulling direction (a lower left direction in FIG. 14, and a left side in FIG. 15 to FIG. 18) respectively relative to the engaged portions 331a and 331b of the corresponding adjustment portions 330a and 330b, and the respective base portions 310a and 310b, and the respective adjustment portions 330a and 330b come close. Namely, the body tissue around the wound moves in such a way as to close the wound. The aforementioned pulling operation is carried out so that the force necessary and sufficient for closing the wound is applied to the body tissue around the wound. By the presences of the engagement claws 336a and 336b, the drawstring portions 320a and 320b can move only in the pulling direction, and cannot move in the opposite direction thereof. That is the same as the case of the closure device 200 described hereinabove.

Such pulling operation of the grip portion 321 (drawstring portions 320a and 320b) is carried out in all of the closure device 300. Thereby, the wound as the closure object is completely closed. Then, in the respective drawstring portions 320a and 320b, the area pulled out beyond the engagement claws 336a and 336b by the pulling operation is cut by the suitable cutting tool. Thereby, the closure of the wound by the closure device 300 is completed.

By maintaining this closure state in the fixed period, the body tissues separated by the wound join each other so that the wound disappears. After that, the base portions 310a and 310b, and the adjustment portions 330a and 330b are removed from the skin.

In the closure device 300 of the present embodiment, it is also easy to modify or finely adjust the separation distance between the respective base portions 310a and 310b and the corresponding adjustment portions 330a and 330b. For example, in a case wherein the drawstring portions 320a and 320b are excessively pulled relative to the adjustment portions 330a and 330b, the drawstring portions 320a and 320b may be removed from the engaged portions 331a and 331b. For this purpose, the drawstring portions 320a and 320b are bent along the respective guide faces 335a and 335b, and in that state, by pulling the drawstring portions 320a and 320b upwardly, the drawstring portions 320a and 320b may pass through respective gaps between the guide faces 335a and 335b and the ceiling walls 337a and 337b. Especially, as mentioned above, the present closure device 300 is disposed in the mirror symmetry in the direction wherein each one of the wall portions 333a and 333b of each one pair of the wall portions 333a, 334a, 333b, and 334b provided in each of the adjustment portions 330a and 330b comes to the proximal position to each other. Consequently, when portions pulled out of the corresponding adjustment portions 330a and 330b in the respective drawstring portions 320a and 320b are bent and deformed in such a way as to come close to each other, the respective drawstring portions 320a and 320b are deformed along the corresponding guide faces 335a and 335b. In that state, by pulling the respective drawstring portions 320a and 320b upwardly, the drawstring portions 320a and 320b can be easily removed from the engaged portions 331a and 331b. In other words, by gripping the respective drawstring portions 320a and 320b from both sides to be bent, and pulling them up in that state, the drawstring portions 320a and 320b can be easily removed from the engaged portions 331a and 331b. Thereby, the adjustment of the separation distance between the base portions 310a and 310b and the adjustment portions 330a and 330b can be carried out desirably.

Then, when the adjustment is completed, the drawstring portions 320a and 320b are disposed between the respective pairs of the wall portions 333a, 334a, 333b, and 334b again from the gaps between the guide faces 335a and 335b and the ceiling walls 337a and 337b. Namely, the concave portions of the drawstring portions 320a and 320b engage the engagement claws 336a and 336b of the engaged portions 331a and 331b, and the separation distances between the base portions 310a and 310b and the corresponding adjustment portions 330a and 330b are fixed. In a case wherein the separation distances between the base portions 310a and 310b and the adjustment portions 330a and 330b are still inadequate, the same adjustment operation may be repeated.

According to the aforementioned closure device 300, since the two drawstring portions 320a and 320b are connected by one grip portion 321, the two drawstring portions 320a and 320b can be simultaneously pulled. Consequently, the wound as the closure object can be swiftly closed.

Also, since the grip portion 321 includes the arch-shaped edge portion 321e, the arch-shaped edge portion 321e is suitably caught on a finger of a user when using the closure device 300 so as to improve the usability.

Furthermore, the present closure device 300 is disposed in the mirror symmetry in the direction wherein each one of the wall portions 333a and 333b of each one pair of the wall portions 333a, 334a, 333b, and 334b provided in each of the adjustment portions 330a and 330b comes to the proximal position to each other. Consequently, by gripping the respective drawstring portions 320a and 320b from both sides to be bent, and pulling them up in that state, the drawstring portions 320a and 320b can be easily removed from the engaged portions 331a and 331b. Thereby, the adjustment of the separation distance between the base portions 310a and 310b and the adjustment portions 330a and 330b can be easily carried out.

Furthermore, even in a case wherein the closure device 300 is used for the joints such as the knee, the elbow, and the like, since the first and second connection pieces 341 and 342 can be bent and deformed, the base portions 310a and 310b and the adjustment portions 330a and 330b can follow the movement of the joint portion.

Also, one closure device 300 is formed by providing respectively two of the base portions 310a and 310b, the adjustment portions 330a and 330b, and the drawstring portions 320a and 320b so as to have a high degree of freedom in arrangement.

Incidentally, in the aforementioned explanation, the closure device 300 including respectively two of the base portions, the adjustment portions, and the drawstring portions has been explained, however, obviously, the closure device 300 may include the aforementioned portions respectively with three or more. For example, in a case wherein the base portions, the adjustment portions, and the drawstring portions are included respectively with four, the closure device 300 can be provided as the closure device wherein two pairs of the aforementioned closure devices 300 are connected through the U-shaped connection pieces. In that case, in the grip portion, all respective tips of the four drawstring portions may be connected at equal intervals, or each respective two adjacent drawstring portions may be connected.

What is claimed is:

1. A closure device for closing a wound in a skin, comprising:
    two closure elements; and
    two sheet materials for integrally disposing the two closure elements,
    wherein each of the closure elements includes a base portion, a drawstring portion integrally extending from the base portion and having engaging portions extending laterally outwardly from two sides of the drawstring portion and a stopper portion raised from an upper surface of the drawstring portion such that the engaging portions are located between the stopper portion and the base portion and extending in a direction perpendicular to a drawing direction of the drawstring, and an adjustment portion through which the drawstring portion passes, the adjustment portion including an engaged portion engaging the engaging portions to allow the drawstring portion to move in one direction and to prevent the drawstring portion to move in an opposite direction opposite to the one direction, and an end so that when the drawstring portion engaging the adjustment portion is pulled in the opposite direction, the stopper portion abuts against the end to prevent the drawstring portion from disengaging from the adjustment portion,
    a base portion of one closure element of the two closure elements, and an adjustment portion of another closure element of the two closure elements are integrally disposed on one sheet material, and
    an adjustment portion of the one of the closure elements, and a base portion of the another of the closure elements are integrally disposed on another sheet material.

2. A closure device according to claim 1, wherein each of the two sheet materials is a surgical tape.

3. A closure device according to claim 1, wherein the adjustment portion further includes a flat plate, a pair of wall portions extending upwardly from the flat plate, each having engagement claws facing each other, as the engaged portion, engaging the engaging portions of the drawstring and sandwiching the drawstring portion between the engagement claws, and a pair of ceiling walls extending from the pair of wall portions to form a space therebetween and located above a part of the flat plate adjacent the engagement claws without covering the engagement claws, the end being formed on the flat plate.

4. A closure device according to claim 3, wherein the drawstring portion further includes a raised portion integrally formed with the stopper portion and raised from an upper surface of the drawstring portion, the space between the pair of ceiling walls being greater than a width of the raised portion but less than a width of the end.

* * * * *